United States Patent [19]

Chung

[11] Patent Number: 5,869,156
[45] Date of Patent: Feb. 9, 1999

[54] POROUS PRODUCTS MANUFACTURED FROM POLYTETRAFLUOROETHYLENE TREATED WITH A PERFLUOROETHER FLUID AND METHOD OF MANUFACTURING SUCH PRODUCTS

[75] Inventor: Hoo Young Chung, Bloomington, Minn.

[73] Assignee: Donaldson Company, Inc., Minneapolis, Minn.

[21] Appl. No.: 852,045

[22] Filed: May 6, 1997

Related U.S. Application Data

[63] Continuation of Ser. No. 289,172, Aug. 10, 1994, abandoned, which is a continuation of Ser. No. 710,501, Jun. 4, 1991, abandoned.

[51] Int. Cl.$^6$ .......................... B01D 39/02; B01D 24/00
[52] U.S. Cl. ................ 428/35.7; 428/36.5; 428/224; 428/304.4; 428/311.1; 428/422; 55/514; 55/522; 55/527; 55/528
[58] Field of Search ................ 428/34.1, 35.7, 428/421, 422, 36.5, 224, 304.4, 311.1; 55/212, 514, DIG. 5, DIG. 45, 522, 528, 527

[56] References Cited

U.S. PATENT DOCUMENTS

| | | | |
|---|---|---|---|
| 2,776,465 | 1/1957 | Smith | 264/175 |
| 2,915,786 | 12/1959 | Haroldson et al. | 264/175 |
| 2,953,428 | 9/1960 | Hunt et al. | 264/210.5 |
| 3,054,761 | 9/1962 | Moore et al. | 524/491 |
| 3,198,691 | 8/1965 | Thomas et al. | 442/164 |
| 3,231,460 | 1/1966 | Andrews | 428/422 |
| 3,265,092 | 8/1966 | Ely et al. | 428/35.1 |
| 3,322,608 | 5/1967 | Mason et al. | 428/150 |
| 3,365,355 | 1/1968 | Netsch | 428/415 |
| 3,391,221 | 7/1968 | Gore et al. | 525/180 |
| 3,407,249 | 10/1968 | Landi | 264/49 |
| 3,486,961 | 12/1969 | Adams | 156/281 |
| 3,513,064 | 5/1970 | Westley | 442/289 |
| 3,664,915 | 5/1972 | Gore | 526/255 |
| 3,783,057 | 1/1974 | McNerney | 526/255 |
| 3,813,461 | 5/1974 | Murayama et al. | 264/41 |
| 3,953,566 | 4/1976 | Gore | 264/505 |
| 3,962,153 | 6/1976 | Gore | 521/79 |
| 4,025,679 | 5/1977 | Denny | 428/91 |
| 4,028,324 | 6/1977 | Tuschner | 260/42.44 |
| 4,031,283 | 6/1977 | Fagan | 442/324 |
| 4,051,011 | 9/1977 | Miyauchi et al. | 264/600 |
| 4,096,227 | 6/1978 | Gore | 264/110 |
| 4,110,392 | 8/1978 | Yamazaki | 264/127 |
| 4,187,390 | 2/1980 | Gore | 174/102 R |
| 4,194,041 | 3/1980 | Gore et al. | 442/289 |
| 4,208,745 | 6/1980 | Okita | 623/1 |
| 4,234,535 | 11/1980 | Okita | 264/519 |
| 4,256,806 | 3/1981 | Snyder | 428/378 |
| 4,283,448 | 8/1981 | Bowman | 428/34.9 |
| 4,321,711 | 3/1982 | Mano | 623/1 |
| 4,321,914 | 3/1982 | Begovac et al. | 128/887 |
| 4,332,035 | 6/1982 | Mano | 623/12 |
| 4,344,999 | 8/1982 | Gohlke | 128/849 |
| 4,385,093 | 5/1983 | Hubis | 428/316.6 |
| 4,443,511 | 4/1984 | Worden et al. | 428/198 |
| 4,478,665 | 10/1984 | Hubis | 156/229 |
| 4,482,516 | 11/1984 | Bowman et al. | 264/127 |
| 4,510,931 | 4/1985 | Henderson et al. | 128/202.28 |
| 4,531,916 | 7/1985 | Scantlebury et al. | 433/173 |
| 4,545,862 | 10/1985 | Gore et al. | 203/10 |
| 4,550,447 | 11/1985 | Seiler, Jr. et al. | 623/1 |
| 4,557,957 | 12/1985 | Manniso | 428/35.8 |
| 4,576,869 | 3/1986 | Malhotra | 428/502 |
| 4,578,063 | 3/1986 | Inman et al. | 604/175 |
| 4,599,810 | 7/1986 | Sacre | 36/55 |
| 4,647,416 | 3/1987 | Seiler, Jr. et al. | 264/118 |
| 4,680,220 | 7/1987 | Johnson | 442/232 |
| 4,718,907 | 1/1988 | Karwoski et al. | 623/12 |
| 4,720,400 | 1/1988 | Manniso | 427/243 |
| 4,743,480 | 5/1988 | Campbell et al. | 428/36.5 |
| 4,747,897 | 5/1988 | Johnson | 156/148 |
| 4,748,217 | 5/1988 | Malhotra | 526/81 |
| 4,770,927 | 9/1988 | Ettenberger et al. | 428/245 |
| 4,816,339 | 3/1989 | Tu et al. | 428/421 |
| 4,822,341 | 4/1989 | Colone | 604/175 |
| 4,869,714 | 9/1989 | Deininger et al. | 600/36 |
| 4,876,051 | 10/1989 | Campbell et al. | 264/127 |
| 4,876,118 | 10/1989 | Wallbillich | 427/142 |
| 4,945,125 | 7/1990 | Dillon et al. | 524/427 |
| 4,955,899 | 9/1990 | Della Corna et al. | 623/1 |
| 5,032,302 | 7/1991 | Juhlke et al. | 252/54 |
| 5,071,609 | 12/1991 | Tuet et al. | 428/422 |
| 5,075,365 | 12/1991 | Wallbillich | 524/261 |
| 5,143,783 | 9/1992 | Shimizu et al. | 428/422 |

FOREIGN PATENT DOCUMENTS

| | | |
|---|---|---|
| 42-13560 | 11/1963 | Japan . |
| 42-13560 | 8/1967 | Japan . |

OTHER PUBLICATIONS

Thornton, James; *Dry, Dry Again*; Corporate Report Minnesota, Feb. 1987, p.41.

Rhodes, Lucien; *The Un–Manager*; Inc., Aug. 1982, p. 24

Brochure; Gore–Tex[198] Membrane Filter Bags; 1980.

Brochure; Gore–Tex[198] Membrane Filter Bag Laminates; 1981.

Brochure; Gore–Tex[198] Membrane Filter Bags & Cartridges; 1981.

Brochure; Gore–Tex[198] Membrane Filter Bags; 1983.

Brochure; Gore–Tex[198] Membrane Filter Bags; 1984.

Brochure; Gore–Tex[198] Membrane Filter Bag Benefits; 1986.

*Primary Examiner*—Rena L. Dye
*Attorney, Agent, or Firm*—Merchant, Gould, Smith, Edell, Welter & Schmidt, P.A.

[57] ABSTRACT

Porous materials suitable for a variety of uses including waterproof/breathable fabrics, air filters, liquid filters, liquid/liquid separation membranes, vascular grafts, mechanical seals, etc. which comprises an intimate combination of about 50 to 99.9 wt % polytetrafluoroethylene polymer and about 0.1 to 50 wt % of a fluorinated organic polymer which is liquid ambient conditions, such as the perfluoroether fluids, in the material has a microstructure characterized by nodes connected by fibrils.

4 Claims, 2 Drawing Sheets

10,000 X 10,000 X

POROUS PRODUCTS MANUFACTURED FROM POLYTETRAFLUOROETHYLENE TREATED WITH A PERFLUOROETHER FLUID AND METHOD OF MANUFACTURING SUCH PRODUCTS

This is a Continuation of application Ser. No. 08/289,172, filed Aug. 10, 1994, now abandoned, which is a continuation of application Ser. No. 07/710,501, filed Jun. 4, 1991 which is now abandoned.

FIELD OF THE INVENTION

The invention broadly relates to porous materials produced by expanding paste-formed polytetrafluoroethylene and methods of manufacturing such materials. Specifically, the invention relates to porous materials produced by either (i) expanding paste-formed polytetrafluoroethylene which has been treated with a fluorinated organic polymer fluid, or (ii) treating expanded paste-formed polytetrafluoroethylene with a fluorinated organic polymer fluid, and methods of manufacturing such materials.

BACKGROUND OF THE INVENTION

Polytetrafluoroethylene is a unique compound commonly employed when one or more of the associated characteristics of chemical inertness, water repellency, and/or electrical insulating value are desired.

Polytetrafluoroethylene can be processed to form a highly porous breathable material which continues to retain the characteristics of chemical inertness, water repellency, and electrical insulating value. Briefly, such porous materials are generally produced by heating and expanding (stretching) a paste-formed body of the polytetrafluoroethylene.

Expanded porous polytetrafluoroethylene films may be used alone or laminated to an assortment of substrates to produce a variety of products including specifically, but not exclusively, sealing thread, breathable/water-repellant fabrics, air filters, liquid filters, vascular grafts (U.S. Pat. Nos. 3,953,566, 3,962,153, 4,208,745, 4,234,535, 4,321,711 4,332,035, 4,550,447, 4,647,416, 4,742,480, and 4,955,899), and numerous others.

Expanded porous polytetrafluoroethylene films have commanded wide acceptance since their introduction because is of their unique combination of properties. However, efforts continue in an attempt to improve upon these properties and thereby increase the potential uses of expanded porous films of polytetrafluoroethylene. One area of concentrated research has been with respect to efforts to increase the radiation resistance of the films, which are notoriously susceptible to degradation by radiation.

Efforts to improve upon the properties and/or uses of porous polytetrafluoroethylene materials by blending an additional component into the polytetrafluoroethylene prior to expansion have met with limited success. In fact, common wisdom in the art advises against incorporation of a matrix interactive component into the polytetrafluoroethylene prior to expansion, except in trace amounts, as a high degree of crystallinity is thought to be necessary to achieve proper expansion of polytetrafluoroethylene and the addition of a matrix interactive component tends to adversely affect the crystallinity.

A singular success in this area is described in U.S. Pat. No. 4,764,560, wherein incorporation of a silicone elastomer into polytetrafluoroethylene resin prior to expansion, followed by polymerization of the silicone elastomer, produces a porous silicone/polytetrafluoroethylene interpenetrating polymeric network having enhanced properties.

Because of the exceptional potential for further unique uses of polytetrafluoroethylene-containing materials, research continues in an effort to improve upon the properties and/or uses of the material.

SUMMARY OF THE INVENTION

Various properties of expanded polytetrafluoroethylene may be created or improved by treating the polytetrafluoroethylene with a fluorinated organic polymer fluid either before or after expansion. The treated expanded porous polytetrafluoroethylene materials possess a microstructure of nodes interconnected by fibrils characteristic of untreated expanded porous polytetrafluoroethylene materials but with fibrils which are substantially free of fissures. As with untreated expanded porous polytetrafluoroethylene materials, the treated materials may be formed in any of a number of desired shapes including films and tubes.

The treated porous polytetrafluoroethylene materials have enhanced resistance to degradation by radiation, enhanced fine particle filtration efficiency, the ability to prevent the passage of methanol, the ability to delay the passage of isopropanol, and an increased elongation to break.

Such treated expanded porous polytetrafluoroethylene materials are suitable for the same uses as untreated expanded porous polytetrafluoroethylene materials including specifically, but not exclusively, waterproof/breathable fabrics for raincoats and tents, air filters for vehicles and computer disk drives, mechanical seals such as bushings and O-rings, liquid filters, and vascular grafts. In addition, the improved properties of the treated porous polytetrafluoroethylene materials permits the treated materials to be used in additional areas such as liquid/liquid separation membranes, and wherever the material would be subject to high levels of radiation.

Specifically, the invention is treating polytetrafluoroethylene with about 0.1 to 50 wt % (preferably 2 to 20 wt %) of a fluorinated organic polymer fluid, such as a perfluoroether fluid, either before or after expansion.

DETAILED DESCRIPTION OF THE INVENTION INCLUDING A BEST MODE

As utilized herein, including the claims, the phrase "fluorinated organic polymer fluid" or "fluorinated fluid" means an organic polymer which is normally liquid under ambient conditions and has a carbon to fluorine mole ratio of less than 2:1 and preferably less than 1.2:1.

As utilized herein, including the claims, the phrase "matrix interactive component" means a component which interacts with and becomes incorporated into the polymeric matrix.

Figure 1:
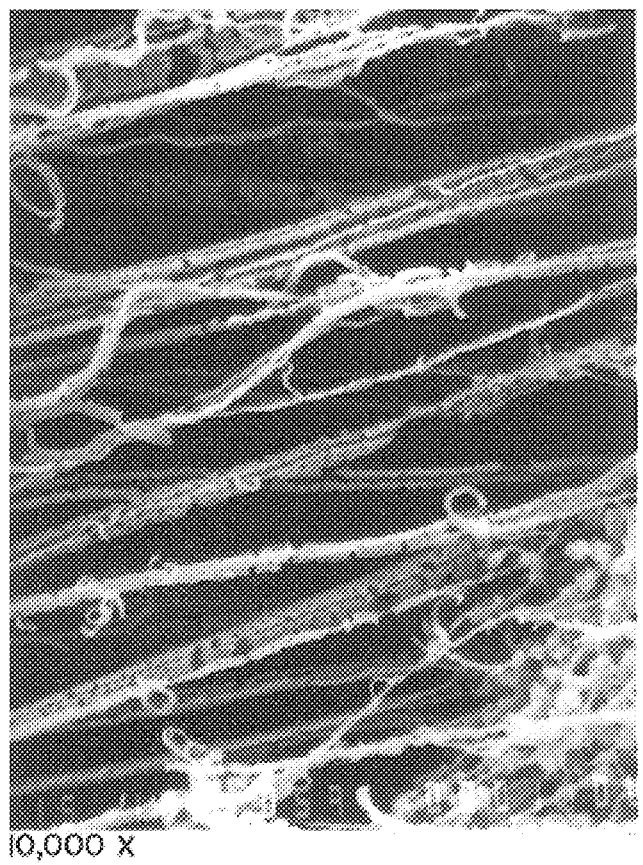
FIG. 1 is a picture of untreated expanded porous polytetrafluoroethylene film stretched 1.25 times in the machine direction and 20 times in the transverse direction taken with an electron microscope at a magnification of X10,000.
Figure 2:
FIG. 2 is a picture of the expanded porous polytetrafluoroethylene film of FIG. 1 after the film was treated with the perfluoroether fluid Fomblin Y 1200™ in accordance with the procedure of Example 2. The picture was taken with an electron microscope at a magnification of X10,000.
Figure 3:
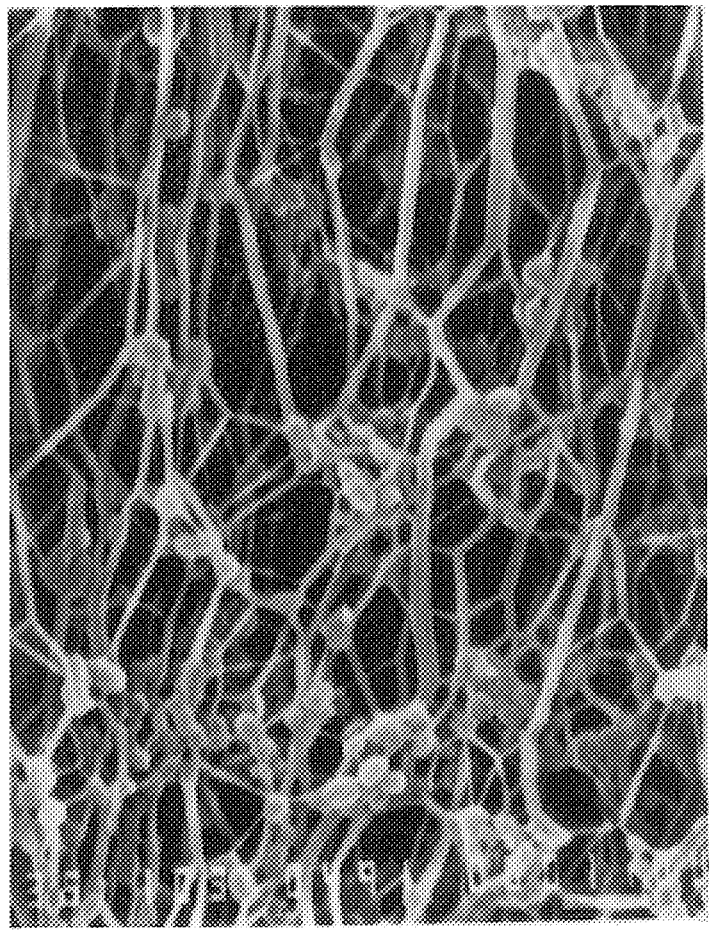
FIG. 3 is a picture of expanded porous polytetrafluoroethylene which was treated with 9 wt % of the perfluoroether fluid Fomblin Y 1200™ prior to stretching and then stretched 1.25 times in the machine direction and 20 times in the transverse direction. The picture was taken with an electron microscope at a magnification of X10,000.

As utilized herein, including the claims, the term "nodule" means a roughly spherical microstructural element from which the nodes of porous expanded polytetrafluoroethylene are formed. Referring to FIGS. 1–3, nodules are independently distinguishable by means of electron scanning microscopy in porous expanded polytetrafluoroethylene.

As utilized herein, including the claims, the phrase "radiation tolerance" refers to the ability to resist degradation when subjected to radiant energy capable of effecting degradation.

As utilized herein, including the claims, the phrase "ultrafine filtration efficiency" refers to filtration efficiency with respect to particles having a particle size of approximately 0.1 microns as measured in accordance with the aerosol testing protocol described in Barris, M. A., Weik T. M., Liu, B. Y., *A Measurement System for High Purity Air Filter Media,* 1986 Institute of Environmental Sciences Proceedings, p. 551.

For purposes of counting the number of separate and distinct nodes in a given area of expanded porous polytetrafluoroethylene, as defined in a photograph of the material taken through electron scanning microscopy, separate and distinct nodes means nodes having at least two physically proximate nodules and no apparent common nodule.

Polytetrafluoroethylene $CF_4(CF_2CF_2)_nCF_4$ is an unusual material commonly manufactured on a commercial scale by dispersion polymerization. Various grades of polytetrafluoroethylene are available from Dupont under the trademark Teflon® and ICC Chemicals under the trademark Fluon®. Some resins have been found to be more suitable for use in the manufacture of expanded porous materials than others. It is generally acknowledged within the art that those grades providing the largest average molecular weight and the highest percentage of crystallinity are preferred for use in the formation of expanded porous materials. In addition, it is generally preferred to utilize a homopolymer of polytetrafluoroethylene. However, it is believed that copolymers of tetrafluoroethylene and another ethylenically unsaturated monomers, such as ethylene, chlorotrifluoroethylene (CTFE), hexafluoropropylene (HFP), perfluoroether containing carboxylic acids, perfluoroether containing sulfonic acids, and the like, may also be suitable for use in the invention when such comonomer is included as a minor component of about 0.001 to about 2 wt % of the polymer matrix.

Because polytetrafluoroethylene has a melt temperature which is above its decomposition temperature, polytetrafluoroethylene may not be melted for molding and shaping as is the common practice for other hydrocarbon resins. For this reason polytetrafluoroethylene is commonly molded and shaped in accordance with a well recognized technique known as paste-forming. Briefly, the paste-forming technique involves mixing the polytetrafluoroethylene resin with a lubricant, typically a volatile hydrocarbon solvent such as kerosene, with subsequent compaction and forming of the mixture to define a cohesive shaped article. The lubricant may be subsequently removed by heating.

The invention is directed to the discovery that a unique porous material with improved properties can be produced by expanding paste-formed polytetrafluoroethylene which has been treated with a fluorinated organic polymer fluid (hereinafter fluorinated fluid) to the polytetrafluoroethylene before or after expansion.

The treated polymeric matrix of polytetrafluoroethylene has the typical microstructure characterized by nodes interconnected by fibrils. However, referring to FIGS. 1–3, a number of significant differences exist between the treated and untreated materials which become clearly discernable when the materials are viewed at a magnification of ten thousand with electron scanning microscopy. The differences include (i) substantially smooth, void-free, continuous surfaces on the fibrils (treated) v. plurality of voids throughout the fibrils (untreated), (ii) multiple parallel strands within each fibril which extend continuously from node to node (treated) v. multiple parallel strands within each fibril which are discontinuous from node to node so as to form voids within the fibril (untreated), and (iii) a substantial increase in the number of independent nodes and fibrils discernable by electron scanning microscopy for a given volume.

Without intending to be limited thereby, I believe that the individual strands are separate crystalline structures bonded together through amorphous regions and that the discontinuity within a strand is the result of a separation along a crystalline interface caused by expansion of the material.

FIGS. 1–3 clearly indicate that treatment of a polytetrafluoroethylene polymer matrix with a fluorinated fluid prior to expansion produces a substantial increase in the density of nodes and fibrils with significantly smaller nodes and significantly shorter fibrils. For example, based upon the method set forth above for counting nodes viewed through electron scanning microscopy, FIGS. 1 (untreated) and 2 (treated after expansion) depict only a fraction of a single node while FIG. 2 (treated before expansion) depicts at least twenty separate and distinct nodes even though the materials were otherwise processed in identical fashion and the pictures were taken at the same magnification and angle.

Generally, it is convenient to incorporate the fluorinated fluid into the polytetra-fluoroethylene resin during the paste-forming process along with the lubricant. While the lubricant is subsequently driven from the porous expanded material, it is believed that the fluorinated fluid remains as a matrix interactive component in the final product as infra red spectra of porous expanded material which has been treated with a fluorinated fluid shows the characteristic peaks associated with the fluorinated fluid. It is theorized that the fluorinated organic polymer can be most effectively blended with the polyteterafluoroethylene by using a supercritical fluid mixing method. For example, it is believed that treatment of polytetrafluoroethylene with a combination of a perfluoroether fluid and $CO_2$, maintained under supercritical conditions, would readily produce an intimate mixture of the polytetrafluoroethylene and the perfluoroether fluid. The intimately blended mixture may then be treated in accordance with the paste-forming technique.

The treated polytetrafluoroethylene may be expanded to form porous materials in accordance with the procedure commonly employed for expanding untreated polytetrafluoroethylene. It is generally believed that the porosity range for materials produced by expanding treated polytetrafluoroethylene will be similar to the porosity range associated with materials produced by expanding untreated polytetrafluoroethylene.

The polytetrafluoroethylene may be treated with about 0.1 to 50 wt % (preferably 2 to 20 wt %) of the fluorinated fluid prior to expansion in order to achieve the desired improved properties. However, the ability to prevent the passage of methanol and isopropanol appears to increase with increasing concentration of the fluorinated fluid such that a fluorinated fluid concentration of at least about 4 wt % is preferred when the porous material is intended for preventing passage of methanol and a fluorinated fluid concentration of at least about 8 wt % is preferred when the porous material is intended for retarding the passage of isopropanol.

Specific fluorinated fluids suitable for use in the invention include: perfluoroether fluids, such as Fomblin® available from Montefluous and Krytox® available from E. I. Dupont DeNemurs; and fluorinated polyalkylene fluids, such as Fluoronert® available from Minnesota Mining and Manufacturing Company. The general chemical formulas of the specified fluids are set forth below:

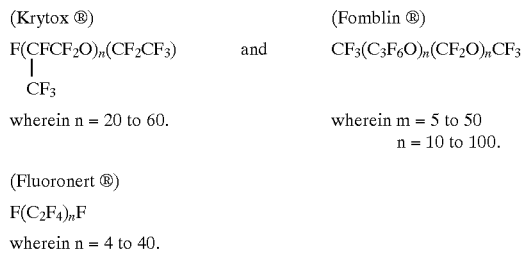

(Krytox ®)

$F(CFCF_2O)_n(CF_2CF_3)$
   |
   $CF_3$ wherein n = 20 to 60.

and (Fomblin ®)

$CF_3(C_3F_6O)_m(CF_2O)_nCF_3$ wherein m = 5 to 50
n = 10 to 100.

(Fluoronert ®)

$F(C_2F_4)_nF$ wherein n = 4 to 40.

Without intending to be limited thereby, I believe that the fluorinated fluid functions on the molecular level to lubricate the crystalline lattice structure of the polytetrafluoroethylene polymeric matrix so as to permit enhanced intercrystalline slippage and thereby achieve improved maintenance of intercrystalline contact when the polytetrafluoroethylene is expanded to form the porous material.

The treated porous polytetrafluoroethylene materials have enhanced resistance to degradation by radiation, enhanced fine particle filtration efficiency, the ability to prevent the passage of methanol, the ability to delay passage of isopropanol, and an increased elongation to break.

The treated expanded porous polytetrafluoroethylene materials are generally suitable for the same uses as untreated expanded porous polytetrafluoroethylene materials. As mention previously, such uses include specifically, but not exclusively, waterproof/breathable fabrics, air filters, liquid filters, vascular grafts, and mechanical seals.

It is believed that the treated expanded porous polytetrafluoroethylene materials can be formulated to have a critical surface tension of less than about 26 dynes/cm (the critical surface tension of homogeneous polytetrafluoroethylene) and generally less than about 23 dynes/cm, so as to be useful for preventing the passage of various hydrocarbons such as methanol.

One of the unique aspects of treated expanded porous polytetrafluoroethylene materials is the ability of the material to permit the passage of gaseous and vaporized substances as well as a variety of liquids having a low critical surface tension, such as acetylene and isopentane, while preventing the passage of a variety of liquids having a relatively high critical surface tension, such as water and methanol.

Tubes formed from the treated expanded porous polytetrafluoroethylene for use as a vascular graft should have an average pore diameter of about 2 to 100 μm, a porosity of about 70% to 95%, an inside diameter of about 1 to 40 mm, and a wall thickness of about 0.3 to 2 mm.

This description is provided to aid in a complete nonlimiting understanding of the invention. Since many variations of the invention may be made without departing from the spirit and scope of the invention, the breadth of the invention resides in the claims hereinafter appended.

EXAMPLES

Expanded Porous Polytetrafluoroethylene Film Treated with Perfluoroether Fluid

Example 1

Into a V-shaped solid-liquid blender manufactured by Patterson Kelly (model #LB-7073) was placed 15 lbs (6.8 kg) Fluon® 123, a finely powdered polytetrafluoroethylene manufactured by ICI. Into the polytetrafluoroethylene was added 1.4 kg kerosene (CAS 64742-47-8) through a side tube in the blender. The combination of finely powdered polytetrafluoroethylene and kerosene was blended for three minutes and then pressed into plugs in accordance with the standard practice for formation of such plugs.

The plugs were ram-extruded into a sheet at a reduction ration of 122.7, calendared to a thickness of 3 mil, and the kerosene volatilized using a series of drying cans.

The resultant formed sheet of polytetrafluoroethylene was transversely stretched approximately 2000% in a tentor frame at a stretch rate of less than 10%/second at a temperature below the melt point of the polytetrafluoroethylene.

Example 2

Expanded porous polytetrafluoroethylene film was manufactured in accordance with the procedure set forth in Example 1. Circular samples having a 4 in (10.2 cm) diameter were cut from the expanded porous polytetrafluoroethylene film and retained between a pair of flexible rings having a three inch (7.6 cm) inside diameter and a four inch (10.2 cm) outside diameter. The retained sample is placed between an air chamber and the atmosphere and air forced through the retained sample from the air chamber to the atmosphere at a rate of 10.5 ft$^3$/min. An aerosol spray of a 50/50 mixture of Fomblin Y 120™, a perfluoroether fluid available from Montefluos, and Freon 113™, a fluorocarbon available from E. I. DuPont DeNemurs, is dispersed within the air chamber at a rate of 0.01 grams/minute for the purpose of exposing the retained sample to the mixture. The retained samples were exposed to the aerosol spray for 5, 10, 30 and 60 minutes.

The aerosol particles were sized and counted with a Laser Aerosol Spectrometer LAS-X™, manufactured by Particle Measurements Systems, Inc. The aerosol was found to contain particles of which more than 90% were found to have a particle size of between 0.1 and 0.4 micrometers.

Example 3

Expanded porous polytetrafluoroethylene film treated with a perfluoroether fluid was manufactured in general accordance with the procedure set forth in Example 1.

Into a V-shaped solid-liquid blender manufactured by Patterson Kelly (model #LB-7073) was placed 6.7 kg CD-123, a finely powdered polytetrafluoroethylene manufactured by ICI United States Inc. Into a separate blender was placed 0.14 kg Fomblin Y 120™, a perfluoroether fluid available from Montefluos, and 1.4 kg kerosene (CAS 64742-47-8) to form a liquid premix. The combination of Fomblin Y 120™ and kerosene was thoroughly agitated and then added to the polytetrafluoroethylene retained within the blender through a side tube in the blender. The combination of finely powdered polytetrafluoroethylene and liquid premix was blended for eight minutes and then pressed into plugs in accordance with the standard practice for formation of such plugs. The ratio of polytetrafluoroethylene to perfluoroether fluid being about 48:1.

The plugs were ram-extruded into a sheet at a reduction ration of 122.7, calendared to a thickness of 3 mil, and the kerosene volatilized using a series of drying cans.

The resultant formed sheet of perfluoroether fluid treated polytetrafluoroethylene was transversely stretched approximately 2000% in a tentor frame at a stretch rate of less than 10%/second at a temperature below the melt point of the polytetrafluoroethylene.

Example 4

The procedure of Example 2 was repeated using 6.44 kg polytetrafluoroethylene and 0.35 kg Fomblin Y 120™ so as to create a polytetrafluoroethylene to perfluoroether fluid ration of about 18:1.

Example 5

The procedure of Example 2 was repeated using 6.44 kg polytetrafluoroethylene and 0.675 kg Fomblin Y 120™ so as to create a polytetrafluoroethylene to perfluoroether fluid ration of about 10:1.

Filtration Efficiency

The filtration efficiency of the expanded porous films manufactured in accordance with Examples 1–5 were measured in accordance with the aerosol testing protocol described in Barris, M. A., Weik T. M., Liu, B. Y., *A Measurement System for High Purity Air Filter Media*, 1986 Institute of Environmental Sciences Proceedings, p. 551. The testing was conducted at a flow rate of 10.5 ft$^3$/ft$^2$/min using liquid DOP particles formed from an alcohol solution. Test results are set forth in Table One below wherein the data represents the average of ten separately tested samples.

TABLE ONE

| Sample | Efficiency | Penetration (10$^{-5}$) |
|---|---|---|
| Example 1 set #1 | 99.9048 | 95.2 |
| Example 1 set #2 | 99.9292 | 70.8 |
| Example 3 set #1 | 99.9985 | 1.5 |
| Example 3 set #2 | 99.9981 | 1.9 |
| Example 4 set #1 | 99.9978 | 2.2 |
| Example 4 set #2 | 99.9902 | 9.8 |
| Example 5 | 99.9980 | 2.0 |

Fluid Resistance

The ability of the expanded porous films of Examples 1, 4 and 5 to resist penetration by various test fluids was measured by covering the opening of a container with a sample of each of the films and placing identically sized drops of test fluids onto the upper surface of each sample using a Pipetman P-1000™ digital microliter pipet manufactured by Rainin Instruments Company. The spread of the test fluid was visually observed and recorded one minute and fifteen minutes after application of the drop. Test fluids included distilled water (73.05 dynes/cm), reagent grade methanol (22.61 dynes/cm), and reagent grade isopropanol (21.7 dynes/cm). Test results are set forth in Table Two below.

TABLE TWO

| Sample | Test Fluid | Time (min) | Observation |
|---|---|---|---|
| Example 1 | Water | 01 | No spreading. |
| | | 15 | No spreading. |
| | Methanol | 01 | Immediate spreading. |
| | Isopropanol | 01 | Immediately spreads across entire membrane. |
| Example 4 | Water | 01 | No spreading. |
| | | 15 | No spreading. |
| | Methanol | 01 | No spreading. |
| | | 15 | No spreading. |
| | Isopropanol | 01 | No spreading. |
| | | 15 | Appreciable spreading. |
| Example 5 | Water | 01 | No spreading. |
| | | 15 | No spreading. |
| | Methanol | 01 | No spreading. |
| | | 15 | No spreading. |
| | Isopropanol | 01 | No spreading. |
| | | 15 | Modest spreading. |

Matrix Tensile Strengths

The tensile strength of expanded porous films manufactured in accordance with the general procedures of Examples 1, 3, 4 and 5 were measured in accordance with ASTM D 882-67 using 1 inch·6 inch samples tested on an Instron model 1000™ tensile tester with a grip separation of 4 inches and a grip separation speed of 2 inches/minute. The matrix tensile strength of the samples was then calculated in accordance with equation 1 set forth below:

$$(213.36 \text{ grams/in}^2) * \frac{(\text{breaking force (lbs}f))}{(\text{specimen weight (grams)})} \quad \text{Eq (\#1)}$$

The constant 213.36 grams/in$^2$ is obtained by multiplying together the specific gravity of polytetrafluoroethylene (2.17 grams/cm$^3$), the length of the test sample (6 inches), and the conversion factor for converting cubic inches to cubic centimeters (16.39 cm$^3$/in$^3$).

Test results are set forth in Table Three below.

TABLE THREE

| Sample | Total Expansion (%) | Stretch Rate (%/sec) | Tensile Strength (psi) | Mass (grams) | Matrix Tensile Strength (psi) |
|---|---|---|---|---|---|
| Example 1 | 14.0 | 06 | | | 8670 |
| Example 1 | 14.0 | 10 | | | 7470 |
| Example 1 | 17.8 | 07 | | | 4380 |
| Example 1 | 19.4 | 08 | | | 6030 |
| Example 1 | 32.6 | 13 | | | 15780 |
| Example 1 | 14.0 | 06 | | | 13200* |
| Example 3 | 14.0 | 06 | | | 7470 |
| Example 3 | 14.0 | 10 | | | 6420 |
| Example 3 | 17.8 | 07 | | | 4220 |
| Example 3 | 19.4 | 08 | | | 7030 |
| Example 3 | 32.6 | 13 | | | 9470 |
| Example 3 | 14.0 | 06 | | | 11400* |
| Example 4 | 17.8 | 07 | | | 4080 |
| Example 4 | 19.4 | 08 | | | 4940 |
| Example 5 | 14.0 | 06 | | | 5020 |
| Example 5 | 14.0 | 10 | | | 3200 |
| Example 5 | 32.6 | 13 | | | 5200 |
| Example 5 | 14.0 | 06 | | | 8650* |

*Sintered by heating above the melt temperature of polytetrafluoroethylene.

Differential Scanning Calorimeter

The melt characteristics of the expanded porous polytetrafluoroethylene films of Examples 1–5 were obtained using a Perkin Elmer DSC-7™ unit with a heating rate of 10° C./minute. Test results are set forth in Table Four below.

It is surprisingly noted that the average melt temperature of the treated expanded porous polytetrafluoroethylene films decreased as the amount of perfluoroether fluid increased and that a single melt temperature peak was obtained for all samples indicating that the perfluoroether fluid was homogeneously dispersed throughout the polytetrafluoroethylene.

TABLE FOUR

| Sample | Temp Range of Peak (°C.) | Average Melt Temp (°C.) |
|---|---|---|
| Example 1 | 345.26–345.84 | 345.38 |
| Example 2 |  | 344.50 |
| Example 3 | 344.08–344.75 | 344.36 |
| Example 4 |  | 344.25 |
| Example 5 | 343.24–344.00 | 343.69 |

Radiation Resistance

The radiation resistivity of films manufactured in accordance with the procedures of Examples 1 (untreated) and 5 (treated) were evaluated by mounting samples onto hollow 8 inch by 10 inch wooden picture frames, exposing the mounted samples to radiation at a level of 2.5 Mrad or 5 Mrad in a Van der Graff-type accelerator for *** hours, and then visually examining the condition of the samples. Test results are set forth in Table Five below.

TABLE FIVE

| Sample | 2.5 Mrad | 5.0 Mrad |
|---|---|---|
| Example 1 | Large Hole | Sample Completely Dissipated |
| Example 5 | Split in the Middle | Large Hole |

I claim:

1. An air filter including a porous polytetrafluoroethylene material; said polytetrafluoroethylene material comprising:
   (a) an expanded, paste-formed polytetrafluoroethylene film having a microstructure of nodes interconnected by fibrils and comprising an intimate blend of:
      (i) 50 to 99.9 wt % polytetrafluoroethylene polymer; and
      (ii) 0.1 to 50 wt % of perfluoroether liquid selected from the group consisting of perfluoroethers according to the general formulae:

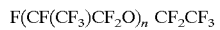

wherein n=5 to 50; and

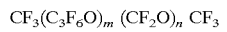

wherein m=5 to 50; and
      wherein n=10 to 100.

2. An air filter according to claim 1 wherein:
   (a) said intimate blend includes at least 4% by weight of said perfluoroether liquid.

3. An air filter according to claim 1 wherein:
   (a) said intimate blend includes at least 8 wt % of said perfluoroether liquid.

4. An air filter according to claim 1, wherein the perfluoroether liquid is present in an amount to provide an increase in the number of independent nodes and fibrils discernible by electron scanning microscopy compared with untreated porous polytetrafluoroethylene material.

* * * * *